(12) United States Patent
White, Jr. et al.

(10) Patent No.: US 10,039,835 B2
(45) Date of Patent: *Aug. 7, 2018

(54) BISMUTH CONTAINING LIQUID PHARMACEUTICAL SUSPENSIONS

(71) Applicant: The Procter & Gamble Company, Cincinnati, OH (US)

(72) Inventors: Daniel Jerome White, Jr., West Chester, OH (US); Michael Selden Godlewski, Loveland, OH (US); Timothy Charles Gulbin, Maineville, OH (US); Graham John Myatt, Manakin Sabot, VA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,445

(22) Filed: Oct. 10, 2016

(65) Prior Publication Data

US 2017/0021027 A1    Jan. 26, 2017

Related U.S. Application Data

(63) Continuation of application No. 14/698,934, filed on Apr. 29, 2015, now Pat. No. 9,486,460.

(60) Provisional application No. 61/985,650, filed on Apr. 29, 2014.

(51) Int. Cl.
| | |
|---|---|
| *A61K 31/60* | (2006.01) |
| *A61K 47/36* | (2006.01) |
| *A61K 47/02* | (2006.01) |
| *A61K 47/12* | (2006.01) |
| *A61K 9/00* | (2006.01) |
| *A61K 47/38* | (2006.01) |
| *A61K 9/08* | (2006.01) |
| *A61K 31/29* | (2006.01) |

(52) U.S. Cl.
CPC ............ *A61K 47/36* (2013.01); *A61K 9/0053* (2013.01); *A61K 9/0095* (2013.01); *A61K 9/08* (2013.01); *A61K 31/29* (2013.01); *A61K 31/60* (2013.01); *A61K 47/02* (2013.01); *A61K 47/12* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,013,560 A * | 5/1991 | Stentz | A61K 9/0095 |
| | | | 424/653 |
| 7,135,197 B2 | 11/2006 | Pena et al. | |
| 8,394,752 B2 | 3/2013 | Erbezci et al. | |
| 2005/0089577 A1 | 4/2005 | Yokoyama et al. | |
| 2008/0227892 A1 | 9/2008 | Van Der Wielen et al. | |
| 2008/0299199 A1* | 12/2008 | Bar-Shalom | A61J 7/0015 |
| | | | 424/484 |
| 2009/0069207 A1 | 3/2009 | Panandiker et al. | |

FOREIGN PATENT DOCUMENTS

| | | | |
|---|---|---|---|
| CN | 102976406 A * | 3/2013 | |
| CN | 102976406 A | 3/2013 | |
| EP | 1 488 812 A1 | 12/2004 | |
| EP | 1488812 A1 * | 12/2004 | ........... A61K 9/0095 |
| FR | 2 703 250 A1 | 10/1994 | |
| GB | 1269987 | 4/1972 | |
| WO | WO 2000/10527 | 3/2000 | |
| WO | WO 0010527 A1 * | 3/2000 | ........... A61K 9/0095 |
| WO | WO 2003/066022 A2 | 8/2003 | |
| WO | WO 03066022 A2 * | 8/2003 | ........... A61K 9/0095 |

OTHER PUBLICATIONS

CN 102976406 A; English Machine Translation—2013.*
International Search Report and Written Opinion for (PCT/US2015/028216) dated Jun. 11, 2015.
All Office Actions for U.S. Appl. No. 14/698,934, filed Apr. 29, 2015.

* cited by examiner

*Primary Examiner* — Jeffrey S Lundgren
*Assistant Examiner* — Michael J Schmitt
(74) *Attorney, Agent, or Firm* — Amanda Herman

(57) ABSTRACT

A liquid pharmaceutical suspension for oral administration containing a bismuth-containing pharmaceutical agent, a suspension system, and water. The suspension system can contain from about 0.001% to about 0.2% gellan gum and from about 0.001% to about 0.75% magnesium aluminum silicate.

20 Claims, 1 Drawing Sheet

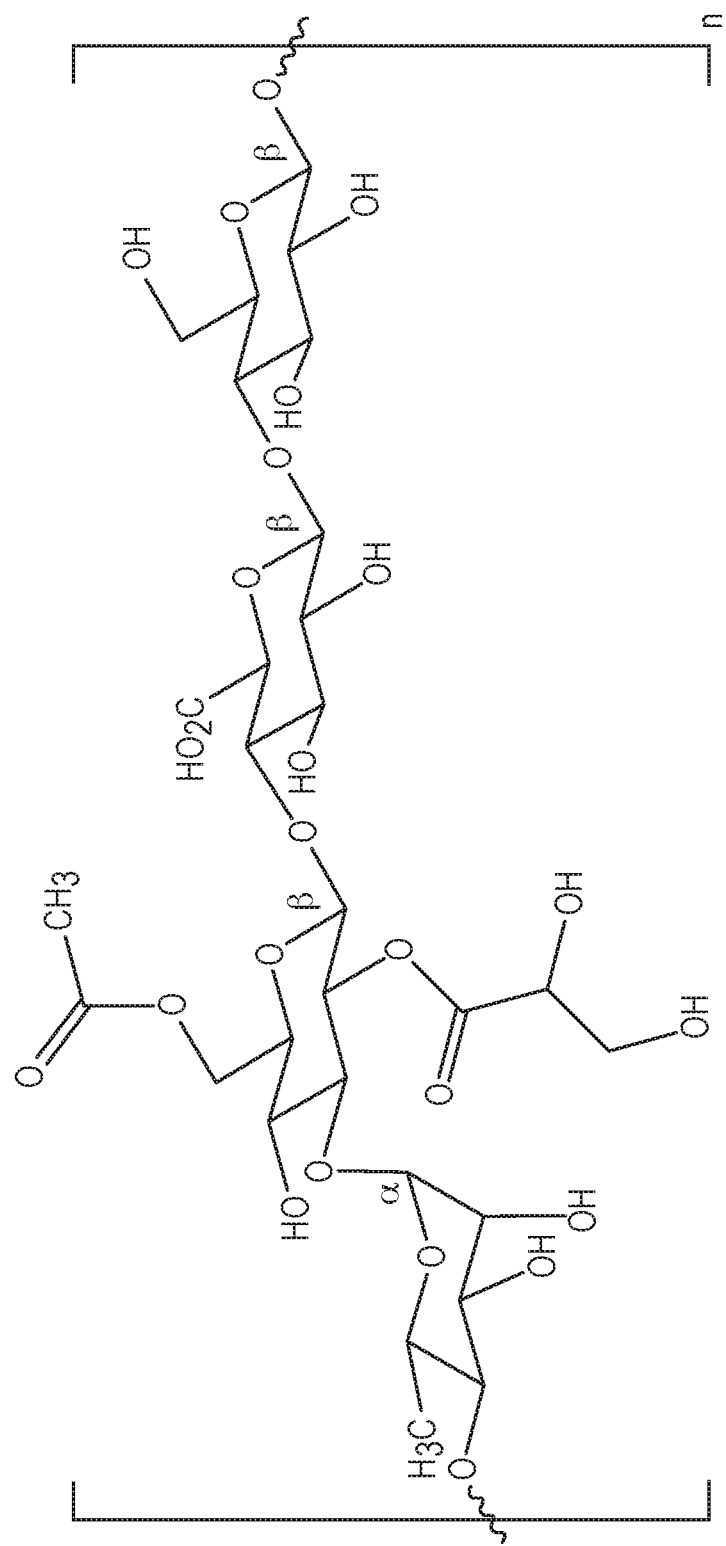

BISMUTH CONTAINING LIQUID PHARMACEUTICAL SUSPENSIONS

FIELD OF THE INVENTION

The present invention relates to liquid pharmaceutical formulations containing bismuth, particularly bismuth-containing pharmaceutical formulations that have improved stability and rheological properties.

BACKGROUND OF THE INVENTION

Bismuth is a common active in over-the-counter liquid pharmaceutical formulations. Pharmaceutical formulations containing bismuth are often sold as suspensions (e.g. Pepto-Bismol®, distributed by Procter & Gamble®) and can be used to treat gastrointestinal symptoms including nausea, heartburn, indigestion, upset stomach, and diarrhea.

It can be difficult to formulate bismuth-containing suspensions that are pH stable, physically stable, and have a rheology that is consumer acceptable. Some currently available formulations exhibit an upward pH drift, shortening the product's shelf-life. Other bismuth-containing liquid formulations can suffer from physical instability and can separate into phases, during storage or under freeze-thaw conditions that can be encountered during shipping and handling, which results in an appearance that is unacceptable to consumers. Furthermore, some consumers do not prefer the rheology of current bismuth products, as the product can have non-uniform viscosities, which can result in an uneven, gloppy, pour, making it more difficult to measure the dose and pour without spilling.

However, it is difficult to improve the stability and rheology of bismuth-containing formulations because small formulation changes can significantly impact the formulation's properties and can even exacerbate the stability and/or rheology problems.

As such, there remains a need for a suspension that has improved pH stability, physical stability, and rheology properties.

SUMMARY OF THE INVENTION

A liquid pharmaceutical suspension for oral administration comprising: (a) a bismuth-containing pharmaceutical agent; (b) a suspension system comprising from about 0.001% to about 0.2% gellan gum and from about 0.001% to about 0.75% magnesium aluminum silicate; (c) water.

A liquid pharmaceutical suspension for oral administration comprising: (a) a bismuth-containing pharmaceutical agent; (b) a suspension system comprising gellan gum; (c) water.

A liquid pharmaceutical suspension for oral administration comprising: (a) a bismuth-containing pharmaceutical agent; (b) a suspension system; (c) water; wherein the formulation comprises less than about 0.2 ppm lead and wherein the liquid formulation has no more than slight sedimentation is visually perceptible after 30 days at 40° C.

BRIEF DESCRIPTION OF THE DRAWING

The FIGURE is a chemical structure of gellan gum.

DETAILED DESCRIPTION OF THE INVENTION

Bismuth-containing pharmaceutical formulations are often sold as suspensions. However, the pH stability, physical stability, and rheology of current formulations can be improved. The current United States Pharmacopeia (USP) Monograph requires that liquid bismuth products have a pH between 3.0 and 5.0. Some current formulations can have an upward pH drift that can decrease their shelf life. Furthermore, current formulations can also have problems with physical stability and can separate into phases during storage and handling, resulting in an appearance that can be undesirable to consumers. To mitigate the physical instability problems, a consumer can shake the bottle to ensure good mixing before use. Bismuth formulations can also have non-uniform viscosities, even after shaking, which can result in an uneven, gloppy, pour, making it more difficult to measure the dose and pour without spilling.

Altering the liquid formulation to improve the stability and rheology can be difficult because even small formulation changes, can negatively affect the taste, mouthfeel, rheology, and pH of the formulation. However, it has been found that making certain adjustments to the excipients, in particular the suspension system, can improve the pH stability, physical stability, and/or rheology of the bismuth formulations.

In one example, it was found that the formulation, particularly the rheology and physical stability, can be improved if the suspension system includes magnesium aluminum silicate, methyl cellulose, and gellan gum. It was surprisingly found that these three components may have a synergistic effect when used in combination. The methyl cellulose can help improve the initial viscosity of the formulation at $0.1\ s^{-1}$ shear rate and a higher initial viscosity can help to improve the formulation's initial physical stability, as well as the physical stability over an extended time. The suspension system can also increase the viscosity of the solution over an extended time. In some examples, the initial viscosity can be higher than the viscosity over an extended time. In some examples, it was found that adding a small amount of magnesium aluminum silicate, can help to make the suspension more stable over an extended period of time. It was also found that consumers thought that formulations which included gellan gum had improved characteristics including mouthfeel, ease of swallowing, smoothness, ease of pour, and aftertaste.

In one example, the bismuth-containing liquid pharmaceutical suspension can contain from about 0.05% to about 0.75% magnesium aluminum silicate, from about 1.5% to about 2.25% methyl cellulose, and from about 0.015% to about 0.5% gellan gum. The liquid-formulation can have an the initial viscosity at $0.1\ s^{-1}$ shear rate of greater than about 2,000 cps and in another example greater than 5,000 cps. The pH drift over 180 days can be from about 0.1 to about 0.8. In one example, the preservative system can contain benzoic acid and optionally sorbic acid.

In another example, it was found that reducing the amount of magnesium aluminum silicate, from the level found in some current formulations, can reduce the upwards pH drift. In one example, the suspension system can contain less than about 0.2% magnesium aluminum silicate and can have a pH drift of less than 0.1 over 180 days.

In another example, the bismuth-containing liquid pharmaceutical suspension can have a suspension system that can include gellan gum and/or methyl cellulose, and no magnesium aluminum silicate and can have a pH drift of less than about 0.1 over 180 days. In one example, the preservative system can contain benzoic acid and optionally sorbic acid.

As used herein, "daily intake" or "permissible daily exposure" refers to the intake level of a nutrient, chemical element, or pharmaceutical active over a 24 hour period.

As used herein, "dose" refers to a volume of the liquid formulation containing an amount of a drug active suitable for administration on a single occasion, according to sound medical practice. A dose can be orally administered and is typically swallowed immediately. In one example, a dose can be about 30 mL, in another example about 25 mL, in another example about 20 mL, in another example about 15 mL, and in another example about 10 mL. The concentration of active ingredients can be adjusted to provide the proper doses of actives given the liquid dose size.

The term "pharmaceutically-acceptable", as used herein, means that the components present in the formulations of the present invention are compatible and suitable for oral administration to a human or mammal. The term "compatible", as used herein, means that the components of the pharmaceutical formulations are capable of being commingled with each other in a manner such that there is no interaction which would substantially reduce the pharmaceutical efficacy of the pharmaceutical formulations, or the effectiveness of the preservatives, under ordinary use situations. Pharmaceutically-acceptable components for use herein must, of course, be of sufficiently high purity and sufficiently low toxicity to render them suitable for oral administration to the human or mammal being treated.

In one example, the liquid medication can contain 525 mg bismuth subsalicylate (BSS) per 30 mL dose. In one example, adults and children 12 years and over can consume one dose (30 mL) every half hour to hour as needed. Users should not ingest more than 8 doses (240 mL) in a twenty-four hour period. Users with diarrhea can follow these directions and use until the diarrhea stops, but not for more than two days. In another example, children under 12 and adults can consume the liquid medication.

In another example, the liquid medication can contain 1050 mg BSS per 30 mL dose. Adults and children 12 years and over can consumer one dose (30 mL) every hour as needed. Users should not ingest more than 4 doses (120 mL) in a twenty-four hour period. In another example, children under 12 and adults can consume the liquid medication.

In one example, the formulation can have a lead level below a certain threshold. The lead level of the formulation and/or the individual components can be measured by any method that satisfies USP <233> Elemental Impurities—Procedures as described in the Second Supplement to USP 35-NF. In one example, the daily intake can be 120 mL and in another example the daily intake can be 240 mL. In one example, the formulation contains less than about 1 ppm lead, in another example less than about 0.7 ppm lead, in another example less about 0.5 ppm lead, in another example less than about 0.4 ppm lead, in another example less than about 0.3 ppm lead, in another example less than about 0.2 ppm lead, in another example less than about 0.1 ppm lead, in another example less than about 0.05 ppm lead, and in another example less than about 0.025 ppm lead. In one example, the formulations can have a daily intake of less than about 40 μg/day lead, in another example less than about 38 μg/day lead, in another example less than about 35 μg/day lead, in another example less than about 30 μg/day lead, in another example less than about 20 μg/day lead, in another example less than about 15 μg/day lead, in another example less than about 10 μg/day lead, and in another example less than about 5 μg/day lead. In one example, the formulations can have a daily intake of less than about 5 μg/day lead. In one example, the liquid formulation contains less than 40 μg lead per 240 mL, in another example less than about 20 μg lead per 240 mL, in another example less than about 10 μg lead per 240 mL, and in another example less than about 5 μg per 240 mL. In one example, the liquid formulation contains less than about 45 μg lead per 120 mL, in another example less than about 30 μg lead per 120 mL, in another example less than about 15 μg per 120 mL, and in another example less than about 5 μg lead per 120 mL. In another example, the volume of liquid formulation that has 4200 mg bismuth contains less than about 40 μg lead, in another example less than about 20 μg lead, in another example less than about 10 μg, and in another example less than about 5 μg lead.

Bismuth-Containing Pharmaceutical Agent

The pharmaceutical formulations of the present invention comprise a bismuth-containing pharmaceutical agent, which can be in the form of a pharmaceutically-acceptable salt. Non-limiting examples of bismuth-containing pharmaceutical agents can include bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. In one example, the pharmaceutical formulation can contain bismuth subsalicylate (BSS).

The liquid pharmaceutical formulations of the present invention can contain from about 0.1% to about 10% of a bismuth-containing pharmaceutical agent, in another example from about 0.5% to about 5%, in another example from about 1% to about 4%, and in another example from about 1.5% to about 2.5%. In another example the formulation can contain from about 0.2% to about 8% of a bismuth-containing pharmaceutical agent, in another example from about 1% to about 6%, and in another example from about 2% to about 4%.

Suspension System

The formulations can also contain a suspension system capable of suspending the bismuth-containing pharmaceutical agent and the other components in an aqueous media.

In one example, the suspension system can contain gellan gum, magnesium aluminum silicate (commercially available as Veegum® and manufactured by Vanderbilt Minerals, LLC), a pharmaceutically-acceptable non-ionic cellulose ether polymer, or mixtures thereof.

In one example, the weight ratio of gellan gum to magnesium aluminum silicate is from about 1.0 to about 0.01, in another example from about 0.8 to about 0.1, in another example from about 0.5 to about 0.01, in another example from about 0.3 to about 0.05, in another example from about 0.25 to about 0.1, and in another example from about 0.15 to about 0.1. In another example, the weight ratio of gellan gum to methyl cellulose is from about 0.01 to about 0.1, in another example from about 0.015 to about 0.05, in another example from about 0.02 to about 0.04, in another example from about 0.025 to about 0.08, and in another example 0.03 to about 0.06. In another example the weight ratio of methyl cellulose to magnesium aluminum silicate is from about 6 to about 15, in another example from about 8 to about 12, and in another example from about 9 to about 11. In another example, the weight ratio of methyl cellulose to magnesium aluminum silicate is from about 1.5 to about 11, in another example from about 2 to about 7, and in another example from about 3.5 to about 6. In another example, the weight ratio of magnesium aluminum silicate to bismuth is from about 0.01 to about 0.5, in another example from about 0.01 to about 0.03, in another example from about 0.01 to about 0.2, in another example from about 0.02 to about 0.15, in another example from about 0.02 to about 0.1, and in another example from about 0.02 to about 0.08. In another example, the weight ratio of magnesium aluminum silicate to bismuth is from about 0.05 to about 0.15.

In one example, the suspending system can have a suspending agent with a high molecular weight. In one example, the molecular weight of the suspending agent is greater than about 500,000 Daltons, in another example greater than about 1 million Daltons, in another example greater than about 1.5 million Daltons, and in another example greater than about 2 million Daltons.

In another example, the suspension system can have a suspending agent that is charged. In one example, the suspension agent can have an anionic charge and in another example the suspension agent can have a cationic charge.

In one example, a suspending agent is gellan gum. The FIGURE shows the chemical structure of gellan gum. The CAS# for gellan gum is 71010-52-1. Gellan gum is a heteropolysaccharide prepared by fermentation of *Pseudomonas elodea* ATCC 31461. Gellan gum is available from Kelco Division of Merck & Co., Inc., San Diego, Calif., under various names, including Kelcogel®.

Gellan gum is a linear, repeating polymer consisting of glucose, rhamnose, and glucuronic acid in the tetrasaccharide repeating unit. It can also exist in either its native high acyl form or a synthetic low acyl form in which all acyl groups have been removed. In the high acyl form of Gellan gum, the glucose portion of the repeating tetrasaccharide unit possesses an acetate and a glycerate group on the same residue. On average, there is one glycerate and 0.5 acetate per repeating tetrasaccharide unit.

In some examples, gellan gum can help create a unique suspension system via the formation of a uniquely functioning "fluid gel" solution with a weak gel structure. In one example, a suspension system that contains gellan gum can also be more physically stable than one without. In one example, liquid formulations that contain a suspension system with gellan gum can have a high, low-shear viscosity, which can provide good suspension properties, even at a low concentration. In another example, gellan gum can help form highly pseudo plastic or thixotropic formulations.

In one example the liquid formulation can contain from about 0.001% to about 0.1% gellan gum, in another example from about 0.005% to about 0.06%, in another example from about 0.01% to about 0.05%, and in another example 0.02% to about 0.04%. In another example the liquid formulation can contain from about 0.007% to about 0.2% gellan gum, in another example from about 0.013% to about 0.17% gellan gum, in another example from about 0.015% to about 0.15% gellan gum, and in another example from about 0.017% to about 0.12% gellan gum. In another example, the composition can contain from about 0.005% to about 1% gellan gum, in another example from about 0.01% to about 0.75% gellan gum, in another example from about 0.16% to about 0.6%, in another example from about 0.2% to about 0.5%, and in another example from about 0.3% to about 0.4%. In one example, the suspension system can contain only gellan gum. In another example, the suspension system can contain only gellan gum and methyl cellulose and in another example the suspension system can contain only gellan gum, methyl cellulose, and magnesium aluminum silicate.

In one example, the suspension system can contain magnesium aluminum silicate, with the chemical formula $Al_2MgO_8Si_2$, which occurs naturally in such smectite minerals as colerainite, saponite, sapphirine, and montmorillonite. Some currently available liquid pharmaceutical suspensions that contain bismuth contain magnesium aluminum silicate, for instance about 1.0% magnesium aluminum silicate. However, formulating with this level of magnesium aluminum silicate can contribute to the upward pH drift and the non-homogenous viscosities. Thus, it can be preferable to formulate with a small amount of magnesium aluminum silicate or even without magnesium aluminum silicate.

In one example, the magnesium aluminum silicate can be made from purified bentonite and thus can have no detectable levels of calcium carbonate. In another example, the magnesium aluminum silicate contains only montmorillonite. In another example, the magnesium aluminum silicate can contain both montmorillonite and saponite.

In one example, the formulation can contain from about 0.001% to about 0.5% magnesium aluminum silicate, in another example from about 0.01% to about 0.25%, in another example from about 0.05% to about 0.2%, and in another example from about 0.075% to about 0.125%. In one example, the formulation can contain from about 0.005% to about 1% magnesium aluminum silicate, in another example from about 0.1% to about 0.8%, in another example from about 0.2% to about 0.6%, and in another example from about 0.3% to about 0.5%. In one example the formulation contains about 1% or less magnesium aluminum silicate, in another example about 0.75% or less, in another example about 0.5% or less, and in another example about 0.4% or less. In one example the formulation contains about 0.3% or less magnesium aluminum silicate, in another example about 0.25% or less, in another example about 0.2% or less, in another example about 0.15% or less, in another example about 0.10% or less, in another example about 0.05% or less. In one example, the formulation is free of magnesium aluminum silicate.

In another example, the suspension system can comprise a non-ionic cellulose ether polymer. Non-limiting examples of non-ionic cellulose ether polymers can be selected from the group consisting of alkylcelluloses (e.g., methyl cellulose), hydroxyalkylalkylcelluloses (e.g., hydroxypropylmethyl cellulose: hydroxybutylmethyl cellulose; hydroxyethylmethyl cellulose; ethylhydroxyethylcellulose), hydroxyalkylcelluloses (e.g., hydroxyethylcellulose; hydroxypropylcellulose), carboxymethyl cellulose sodium, microcrystalline cellulose, a combination of carboxymethyl cellulose sodium and microcrystalline cellulose (e.g. Avicel RC-591 of FMC Corp.), and mixtures thereof. In one example, the formulation can contain alkylcelluloses. In one example, the formulation can contain methyl cellulose. In one example, the formulation can contain from about 0.1% to about 5% non-ionic cellulose ethyl polymer, in another example from about 0.1% to about 3%, in another example from about 0.5% to about 1.5%, and in another example from about 0.75% to about 1.3%.

In another example, the suspension system can include a component selected from the group consisting of carboxymethyl cellulose sodium, microcrystalline cellulose, a combination of carboxymethyl cellulose sodium and microcrystalline cellulose, xanthan gum, silicon dioxide, and mixtures thereof.

In another example, the suspension system can contain xanthan gum. Since xanthan gum is a high molecular weight polysaccharide produced through pure culture fermentation of carbohydrates by the microorganism *Xanthomonas camoestris*, it does not contain measurable quantities of lead. In one example, the formulation can contain from about 0.1% to about 5% xanthan gum, in another example from about 0.1% to about 3%, and in another example from about 0.5% to about 1.5%.

In another example, the suspension system can include a synthetic clay.

In another example, the suspension system can contain a synthetic clay, such as lithium magnesium sodium silicate (commercially available as Laponite™ from BYK-Chemie GmbH, Germany) Non-limiting examples of synthetic clays can include lithium magnesium silicate, lithium magnesium sodium silicate, and combinations thereof.

In another example, the suspension system can include bentonite, which are absorbent aluminum phyllosilicates.

In another example the suspension system can include clay minerals selected from the kaolin group which can include the minerals kaolinite, dickite, halloysite, and/or nacrite; the smectite group which can include dioctahedral smectites such as montmorillonite, nontronite, and/or trioctahedral smectites; the illite group which can include clay-micas; the chlorite group; attapulgite clays; sepiolite; and combinations thereof.

In another example, the suspension system can contain less than about 20 ppm lead, in another example less than about 15 ppm lead, in another example less than about 10 ppm lead, in another example less than 7 ppm lead, and in another example less than 5 ppm lead. In one example the suspension system can contain from about 1 ppm lead to about 13 ppm lead, in another example from about 5 ppm to about 11 ppm lead, and in another example from about 6.5 ppm lead to about 9.5 ppm lead.

Buffers

The liquid pharmaceutical formulation can contain a buffer. The buffer can help keep the pH within a desired range. The pH of the formulation can be from about 3.0 to about 5.0. The pH can be measured using the pH Method, described hereafter.

The initial pH, which can be measured soon after the formulation is made, can be from about 3 to about 4.2, in another example from about 3.05 to about 3.7, in another example from about 3.1 to about 3.4, and in another example from about 3.1 to about 3.3. The 36 day pH can be from about 3.0 to about 4.5, in another example from about 3.1 to about 4.0, in another example from about 3.1 to about 3.8, and in another example from about 3.2 to about 3.4. The 36 day pH is measured after the formulation is stored in a closed PET bottle for 36 days at ambient temperature out of direct sunlight.

In one example, the formulations can have an upward pH drift, when comparing the change in pH from the pH at 36 days to the initial pH. In one example, the pH change over 36 days is from about 0.02 to about 0.5, in another example from about 0.05 to about 0.4, and in another example from about 0.1 to about 0.3. In one example, the pH change over 36 days is less than about 0.4, in another example less than about 0.3, in another example less than about 0.2, and in another example less than about 0.1. In another example, the pH change over 36 days is greater than about 0, in another example greater than about 0.03, in another example greater than about 0.1, and in another example greater than about 0.18. The pH can be determined by the pH Test Method, described hereafter.

In one example, the pH change over 180 days is from about 0.02 to about 1, in another example from about 0.1 to about 0.8, and in another example from about 0.2 to about 0.6. In one example, the pH change over 180 days is less than about 0.9, in another example less than about 0.7, in another example less than about 0.6, in another example less than about 0.5, in another example less than about 0.3, and in another example less than about 0.1. In another example, the pH change over 180 days is greater than about 0, in another example greater than about 0.15, and in another example greater than about 0.3. The pH can be determined by the pH Test Method, described hereafter.

In one example the liquid medication can contain from about 0.001% to about 1% buffer, in another example from about 0.01% to about 0.5% buffer, in another example from about 0.02% to about 0.3% buffer, and in another example from about 0.05% to about 0.15% buffer. Non-limiting examples of buffers can include acetic acid, sodium acetate, citric acid, sodium citrate, monobasic sodium phosphate, dibasic sodium phosphate, sodium carbonate, sodium bicarbonate, succinic acid, sodium succinate, potassium dihydrogen phosphate, phosphoric acid, salicylic acid, and combinations thereof.

In another example, the buffer can contain salicylic acid. In one example the formulation can contain from about 0.01% to about 0.5% salicylic acid, in another example from about 0.03 to about 0.25%, and in another example 0.05% to about 0.1%.

Preservative

The liquid pharmaceutical formulation can contain a preservative. Non-limiting examples of preservatives can include benzalkonium chloride, ethylenediaminetetraacetic acid (EDTA), benzyl alcohol, potassium sorbate, parabens, benzoic acid, sorbic acid, sodium benzoate, and mixtures thereof. The formulation can contain from about 0.01% to about 0.5% preservative, in another example from about 0.02% to about 0.1%, and in another example from about 0.03% to about 0.05%.

In one example, the liquid pharmaceutical formulation can contain benzoic acid or a pharmaceutically-acceptable salt of benzoic acid. In one example the formulation can contain from about 0.01% to about 0.2% benzoic acid, in another example from about 0.01% to about 0.1%, and in another example from about 0.015% to about 0.03%. In one example, the only buffer in the formulation can be benzoic acid.

In another example, the liquid pharmaceutical formulation can contain sorbic acid or a pharmaceutically-acceptable salt of sorbic acid. In one example the formulation can contain from about 0.01% to about 0.1% sorbic acid, in another example from about 0.01% to about 0.08%, in another example from about 0.01% to about 0.04%, and in another example from about 0.0125% to about 0.04%.

In one example, the only preservative in the formulation can be benzoic acid. In another example, the formulation can contain two preservatives, sorbic acid and benzoic acid.

Water

The liquid formulations of the present invention can further comprise from about 80% to about 99% water, in another example from about 90% to about 99%, and in another example from about 93% to about 98%.

Optional Components

In addition to the components described hereinbefore, the pharmaceutical formulations can contain additional optional components selected as appropriate for the particular formulation being prepared. The choice of pharmaceutically-acceptable optional components to be used in the formulations of the present invention is basically determined by the properties, especially aesthetic properties, desired for the formulation. Pharmaceutically-acceptable optional components suitable for the preparation of formulations herein for oral administration are well known in the art.

Some examples of substances that can serve as pharmaceutically-acceptable optional components are sugars such as lactose, glucose and sucrose; non-nutritive sweeteners such as saccharin, aspartame, acesulfame, sucralose, and cyclamate; coloring agents; flavoring agents such as methyl salicylate, peppermint and cherry flavor; etc. In one example, the sweetener is sucralose. In another example, the sweetener does not contain saccharin.

Other compatible pharmaceutical additives and actives (e.g., non-steroidal anti-inflammatory drugs such as aspirin, ibuprofen, and naproxen; acetaminophen; $H_2$ receptor antagonists; antacids) may be included in the pharmaceutically-acceptable optional components for use in the formulations of the present invention.

In another example, the bismuth-containing formulation has less than 25 ppm cadmium per daily intake, less than 15 ppm inorganic arsenic per daily intake, less than 15 ppm inorganic mercury per daily intake, less than 100 ppm iridium, osmium, palladium, platinum, rhodium, ruthenium, or molybdenum per daily intake, and/or less than 500 ppm nickel per daily intake. Additional information on elemental impurities can be found in USP <232> Elemental Impurities—Limits as described in Second Supplement to USP 35-NF. The level of elemental impurities in the formulation and/or the individual components can be measured by any method that satisfies USP <233> Elemental Impurities—Procedures as described in the Second Supplement to USP 35-NF.

Examples

For the following examples, the methyl cellulose was supplied by Hercules Aqualon a subsidiary of Ashland®, Inc. (Wayne, N.J.). The magnesium aluminum silicate is commercially available as Veegum® HV from Vanderbilt Minerals, LLC (Murray, Ky., USA), unless it is specified that it is Veegum® N, which is also available from Vanderbilt Minerals. The gellan gum is commercially available as Kelogel® CG-HA from CP Kelco (Atlanta, Ga.).

Examples 1-10, 18-19, and A-Q were made as follows. First, three premixes or slurries were made. The dye premix was made by adding color to water and heating and stirring until dissolved.

Separately, a minors premix was made by adding the flavor, salicylic acid, sodium salicylate, sweeteners, benzoic acid, and sorbic acid to water and heating and stirring until the solution became clear.

Separately, a BSS slurry was made by adding BSS powder to water under high shear.

To make the examples, the first step was to add the suspension system components to water. Each suspension system component, if present, was added to water under high shear mixing: magnesium aluminum silicate, methyl cellulose, and finally gellan gum. Then, under low shear mixing the dye premix, the BSS slurry, and the minors premix were added. Then Q.S. of water was added to form the final bismuth-containing pharmaceutical formulation.

In the first example, a taste test was performed with 10 male consumer panelists. Each panelist ingested 30 mL of five blinded samples in a randomized order. Four of the samples correspond to Examples 1 to 4, as described below in Table 1B, and one commercial product was used, Pepto-Bismol®. All samples were original flavor and regular strength. Each panelist sampled one example per day for five days.

Panelists poured a 30 mL dose from a container and then ingested the dose Immediately following ingestion, panelists completed a questionnaire where they rated the product they had just tasted for overall rating and liking as well as various characteristics. Panelists also rated the aftertaste 15 and 30 minutes after ingesting the product. Panelists were instructed not to eat or drink anything other than water until after they had completed the questions related to aftertaste.

The panelists gave each formulation a qualitative rating of excellent, very good, good, fair, or poor based on his overall rating based on perception and taste of the sample. Then, the ratings were converted to a numerical value and the mean was calculated. An excellent rating scored 100, very good scored 75, good scored 50, fair scored 25, and poor scored 0.

The average overall rating and average ratings for each characteristic can be seen in Table 1A, below.

TABLE 1A

| | Ex. 1 | Ex. 2 | Ex. 3 | Ex. 4 | Ex. 5 Current Pepto[1] |
|---|---|---|---|---|---|
| Overall Rating | 67.5 | 45.0 | 70.0 | 57.5 | 60.0 |
| Overall Mouth Feel | 62.5 | 52.5 | 62.5 | 62.5 | 57.5 |
| Ease of Swallow | 67.5 | 57.5 | 70.0 | 70.0 | 60.0 |
| Chalkiness Level | 52.5 | 62.5 | 60.0 | 66.7 | 62.5 |
| Thickness | 55.0 | 47.5 | 57.5 | 55 | 62.5 |
| Smoothness | 75.0 | 65.0 | 70.0 | 70.0 | 55.0 |
| Coating of Throat | 56.2 | 66.7 | 58.3 | 61.1 | 63.9 |
| Overall Appearance | 67.5 | 57.5 | 65.0 | 66.7 | 52.5 |
| Ease of Pour | 70.0 | 65.0 | 67.5 | 70.0 | 55.0 |
| Overall Flavor | 62.5 | 50.0 | 62.5 | 47.2 | 67.5 |
| Aftertaste | 55.0 | 47.5 | 62.5 | 44.4 | 57.5 |
| Odor | 65.0 | 62.5 | 65.0 | 58.3 | 67.5 |
| Sourness | 55.0 | 45.0 | 50.0 | 37.5 | 57.5 |
| Sweetness | 55.0 | 55.0 | 55.0 | 45.0 | 60.0 |

[1]Lot # 2296 171951, Expiration September 2014

TABLE 1B

| | Ex. 1 | Ex. 2 | Ex. 3 | Ex. 4 |
|---|---|---|---|---|
| BSS | 1.7305% | 1.7305% | 1.7305% | 1.7305% |
| Methyl cellulose | 1.086% | 1.086% | 1.086% | 1.086% |
| Magnesium aluminum silicate | 0% | 0% | 0.1% | 0% |
| Magnesium aluminum silicate[2] | 0.9924% | 0% | 0% | 0% |
| Gellan gum | 0% | 0.05% | 0.025% | 0.0375% |
| Benzoic Acid | 0.025% | 0.025% | 0.025% | 0.025% |
| Sorbic Acid | 0.0126% | 0.0126% | 0.0126% | 0.0126% |
| Salicylic acid | 0.071% | 0.071% | 0.071% | 0.071% |
| Sweetener | 0.0604% | 0.0604% | 0.0604% | 0.0604% |
| Color | 0.0124% | 0.0124% | 0.0124% | 0.0124% |
| Flavor | 0.0888% | 0.0888% | 0.0888% | 0.0888% |
| Distilled Water | Q.S. | Q.S. | Q.S. | Q.S. |
| Initial pH (neat) | 3.67 | 3.09 | 3.17 | 3.07 |
| 36 day pH (ambient storage, neat) | 4.09 | 3.13 | 3.37 | 3.12 |
| Change in pH (36 day pH − initial pH) | 0.42 | 0.04 | 0.20 | 0.05 |

[2]Commercially available as Veegum® N

Example 3 had an improved overall experience versus commercial Pepto-Bismol®. This formula was rated directionally higher than the commercial control overall and for mouthfeel, ease of swallowing, smoothness, ease of pour, and aftertaste. Example 4 was perceived similarly to Example 3 for mouthfeel, ease of swallowing, etc., however had lower ratings for overall flavor, aftertaste, odor, sourness, and sweetness. Thus, adding 0.1% magnesium aluminum silicate can favorably impact the overall experience of the liquid medication.

A second taste test was performed with 116 consumer panelists (43% male, 57% female, aged 22 to 59). In this test, each panelist ingested 30 mL of five blinded samples in a randomized order. Three of the samples correspond to Examples 6, 7, and 8, as described below in Table 2B, and two commercial products were used, Pepto-Bismol® and Kroger® Liquid Stomach Relief. All samples were original flavor and regular strength. Panelists were given twelve days to complete the panel and almost all panelists tasted one sample per day with the exception of eight panelists who tasted two samples in a day.

The test was done approximately the same as described above, except each panelist was given 40 mL of the sample in a small cup and asked to measure a 30 mL dose into a standard dose cup and then ingest the 30 mL dose Immediately following ingestion, panelists completed the same questionnaire as described above.

The average overall rating and average ratings for each characteristic can be seen in Table 2A, below.

TABLE 2A

|  | Ex. 6 | Ex. 7 | Ex. 8 | Ex. 9 Pepto-Bismol®[3] | Ex. 10 Kroger® Liquid Stomach Relief[4] |
|---|---|---|---|---|---|
| Overall Rating | 45 | 62 | 54 | 53 | 49 |
| Overall Mouth Feel | 49 | 63 | 60 | 54 | 49 |
| Ease of Swallow | 61 | 71 | 64 | 61 | 58 |
| Chalkiness Level | 48 | 60 | 55 | 50 | 41 |
| Thickness | 51 | 61 | 57 | 53 | 50 |
| Smoothness | 57 | 68 | 63 | 61 | 60 |
| Coating of Throat | 54 | 64 | 62 | 59 | 57 |
| Overall Appearance | 39 | 63 | 56 | 49 | 43 |
| Ease of Pour | 59 | 64 | 65 | 60 | 60 |
| Overall Flavor | 39 | 63 | 56 | 49 | 43 |
| Aftertaste | 41 | 54 | 50 | 43 | 39 |
| Odor | 57 | 65 | 64 | 56 | 57 |
| Sourness | 43 | 61 | 54 | 51 | 48 |
| Sweetness | 45 | 65 | 58 | 54 | 45 |

[3]Lot # 2296 171951, Expiration September 2014
[4]Lot #AK0329

TABLE 2B

|  | Ex. 6 | Ex. 7 | Ex. 8 |
|---|---|---|---|
| BSS | 1.7305% | 1.7305% | 1.7305% |
| Methyl cellulose | 1.0860% | 1.0860% | 1.0860% |
| Magnesium aluminum silicate | 0.1000% | 0.1000% | 0% |
| Gellan gum | 0.0250% | 0.0250% | 0.0375% |
| Benzoic Acid | 0.0250% | 0.0250% | 0.0250% |
| Sorbic Acid | 0.0126% | 0.0126% | 0.0126% |
| Salicylic acid | 0.0594% | 0.0594% | 0.0594% |
| Sodium Salicylate | 0.0738% | 0.0738% | 0.0738% |
| Sweetener | 0.0612% | 0.0612% | 0.0612% |
| Color | 0.0124% | 0.0124% | 0.0124% |
| Flavor | 0.0888% | 0.0888% | 0.0888% |
| Distilled Water | Q.S. | Q.S. | Q.S. |

Example 7 had the highest overall rating by the panelists and also ranked the highest for most of the other product characteristics. Furthermore, Example 7 was perceived as being approximately equal to or more favorable for all characteristics when compared to current Pepto-Bismol®. In particular, Example 7 was rated less chalky, less aftertaste, less sour, and better overall flavor than current Pepto-Bismol®. Example 8, which did not have magnesium aluminum silicate, was less desirable by consumers than Example 7 and had a less desirable taste and the components also fell out of the suspension.

The next example compares the initial viscosity of compositions with different suspension systems. The initial viscosity, in particular the initial viscosity at $0.1\ s^{-1}$, affects the physical stability of the liquid pharmaceutical composition. A higher initial viscosity at $0.1\ s^{-1}$ shear rate can improve the formulation's physical stability.

Some current liquid bismuth formulations have a suspension system that contains magnesium aluminum silicate and methyl cellulose and can exhibit low level physical instability. This means that after about three to six months of storage, a clear ring can form at the top of the liquid and a precipitate of large clusters of bismuth crystals can collect at the bottom of the bottle. Although, consumers can shake the bottle to ensure good mixing before ingesting the contents, the bismuth formulations can look less appealing on the store shelf or inside the consumer's medicine cabinet. Furthermore, the separation, even after shaking, can cause the liquid composition to have non-uniform viscosities which can result in an uneven, gloppy, pour, making it more difficult to measure the dose and pour without spilling and unpleasant mouthfeel.

Table 3A, below, shows the formulations for Examples 11-17. Examples 11-17 do not contain actives or additional excipients. Examples 11-17 were made by adding each component of the suspension system to water under high shear mixing. Then, Q.S. of water was added to form the final formulation.

Table 3B, below, shows the initial viscosity of Examples 11-17 at different shear rates. The materials added in Table 3A, correspond to the suspension system of the finished product in Table 3B.

TABLE 3A

| | Materials Added | | | |
|---|---|---|---|---|
| Example | Magnesium aluminum silicate (%) | Gellan gum (%) | Methyl cellulose (%) | Distilled Water (%) |
| 11 | 0.22 | 0 | 0 | Q.S. |
| 12 | 0 | 0.06 | 0 | Q.S. |
| 13 | 0 | 0 | 2.36 | Q.S. |
| 14 | 0.22 | 0.06 | 0 | Q.S. |
| 15 | 0.22 | 0 | 2.35 | Q.S. |
| 16 | 0 | 0.05 | 2.36 | Q.S. |
| 17 | 0.22 | 0.05 | 2.35 | Q.S. |

TABLE 3B

| | Suspension System of Finished Product | | | 25° C. Initial Viscosity (cps) | | | | |
|---|---|---|---|---|---|---|---|---|
| Example | Magnesium aluminum silicate (%) | Gellan gum (%) | Methyl cellulose (%) | $0.1\ s^{-1}$ | $1\ s^{-1}$ | $10\ s^{-1}$ | $20\ s^{-1}$ | $100\ s^{-1}$ |
| 11 | 0.1 | 0 | 0 | 7 | 1 | 1 | 1 | 1 |
| 12 | 0 | 0.25 | 0 | 268 | 125 | 47 | 33 | 14 |

TABLE 3B-continued

| | Suspension System of Finished Product | | | 25° C. Initial Viscosity (cps) | | | | |
|---|---|---|---|---|---|---|---|---|
| Example | Magnesium aluminum silicate (%) | Gellan gum (%) | Methyl cellulose (%) | 0.1 s$^{-1}$ | 1 s$^{-1}$ | 10 s$^{-1}$ | 20 s$^{-1}$ | 100 s$^{-1}$ |
| 13 | 0 | 0 | 1.086 | 3712 | 2774 | 1591 | 1286 | 734 |
| 14 | 0.1 | 0.25 | 0 | 667 | 173 | 49 | 34 | 14 |
| 15 | 0.1 | 0 | 1.086 | 5185 | 3780 | 2041 | 1619 | 887 |
| 16 | 0 | 0.25 | 1.086 | 18780 | 7446 | 2901 | 2165 | 1052 |
| 17 | 0.1 | 0.25 | 1.086 | 33110 | 11980 | 4147 | 2984 | 1405 |

Surprisingly, the suspension system in Example 17, which is equivalent to a finished product containing 0.1% magnesium aluminum silicate, 0.025% gellan gum, 1.086% methyl cellulose, had the highest initial viscosity at 0.1 s$^{-1}$. This value was significantly higher than any other suspension system tested, which indicates that there may be a synergistic effect when these three components are used in a suspension system.

Furthermore, Example 13, where the suspension system only contains methyl cellulose, is significantly higher than Examples 11 and 12, where the suspension system only contains magnesium aluminum silicate and gellan gum, respectively. However, when methyl cellulose is combined with a small amount of magnesium aluminum silicate, as in Example 15, or gellan gum, as in Example 16, the initial viscosity at 0.1 s$^{-1}$ shear rate is significantly higher than methyl cellulose alone.

It is also surprising that gellan gum had only a slight effect on the formulation's initial viscosity in the mid to high shear range (greater than or equal to 10 s$^{-1}$ shear rate) but had a large effect on the initial low shear (0 s$^{-1}$ shear rate to 1 s$^{-1}$ shear rate).

In one example, the initial viscosity at 0.1 s$^{-1}$ shear rate is greater than about 1000 cps, in another example greater than about 2000 cps, in another example greater than about 3000 cps, in another example greater than about 3500 cps, in another example greater than about 4000 cps, in another example greater than about 4500 cps, in another example greater than about 5000 cps, in another example greater than about 10,000 cps, in another example greater than about 15,000 cps, in another example greater than about 18,500 cps, in another example greater than about 19,000 cps, in another example greater than about 21,000 cps, in another example greater than about 25,000 cps, in another example greater than about 28,000 cps, in another example greater than about 30,000 cps, and in another example greater than about 32,000 cps. In another example, the initial viscosity at 0.1 s$^{-1}$ shear rate is from about 5000 cps to about 40,000 cps, in another example from about 8,000 cps to about 37,000 cps, in another example from about 10,000 cps to about 35,000 cps, and in another example from about 18,000 cps to about 33,500 cps. In another example, the initial viscosity at 0.1 s$^{-1}$ shear rate is from about 1000 cps to about 26,000 cps, in another example from about 2,000 cps to about 15,000 cps, in another example from about 4,000 cps to about 10,000 cps, and in another example from about 5,000 cps to about 6,000 cps. The initial viscosity can be determined by the Rheology Test Method, described hereafter.

In another example, the viscosity throughout the shelf life of the composition at 0.1 s$^{-1}$ shear rate is greater than about 100 cps, in another example greater than 250 cps, in another example greater than about 500 cps, in another example greater than about 750 cps, in another example greater than about 1000 cps, in another example greater than about 2000 cps, in another example greater than about 4000 cps, in another example greater than about 5000 cps, in another example greater than about 7000 cps, and in another example greater than about 10,000 cps. In another example, the viscosity at the end of the shelf life at 0.1 s$^{-1}$ shear rate can be from about 500 cps to about 15,000 cps, in another example from about 1000 cps to about 13,000 cps, in another example from about 3000 cps to about 9,000 cps, and in another example from about 4000 cps to about 7000 cps. The initial viscosity can be determined by the Rheology Test Method, described hereafter.

Table 4A, below, shows the sedimentation after 30 days at 40° C. of formulations with varying suspension systems. Table 4B, below, shows the composition of Examples A-Q.

TABLE 4A

| | Suspension System | | | |
|---|---|---|---|---|
| Example | Magnesium aluminum silicate (%) | Gellan gum (%) | Methyl cellulose (%) | Description of Sedimentation after 30 days at 40° C. |
| A | 0.1 | 0.025 | 1.086 | Slight sediment |
| B | 0.1 | 0.025 | 1.3 | Slight sediment |
| C | 0.1 | 0.03 | 1.193 | Slight sediment |
| D | 0.1 | 0.035 | 1.3 | No sediment |
| E | 0.1 | 0.035 | 1.086 | Slight sediment |
| F | 0.125 | 0.025 | 1.193 | Very slight sediment |
| G | 0.125 | 0.03 | 1.086 | No sediment |
| H | 0.125 | 0.03 | 1.193 | No sediment |
| I | 0.125 | 0.03 | 1.3 | No sediment |
| J | 0.125 | 0.03 | 1.193 | Slight sediment |
| K | 0.125 | 0.035 | 1.193 | No sediment |
| L | 0.15 | 0.025 | 1.086 | No sediment |
| M | 0.15 | 0.025 | 1.3 | No sediment |
| N | 0.15 | 0.025 | 1.086 | No sediment |
| O | 0.15 | 0.03 | 1.193 | No sediment |
| P | 0.15 | 0.035 | 1.3 | No sediment |
| Q | 0.15 | 0.035 | 1.086 | Slight sediment |

TABLE 4B

|  | Examples A-Q |
|---|---|
| BSS | 1.7305% |
| Suspension System | See Table 4A |
| Benzoic Acid | 0.025% |
| Salicylic Acid | 0.0749% |
| Sodium Salicylate | 0.0559% |
| Sweetener | 0.0612% |
| Color | 0.0124% |
| Flavor | 0.088% |
| Distilled Water | Q.S. |

Table 4A shows that even though methyl cellulose had the largest effect on the formulation's initial viscosity, it may not provide physical stability with respect to the suspension. However, if the formulation includes a low level of magnesium aluminum silicate, the formulation can have better suspension stability. This is especially surprising because magnesium aluminum silicate had very little effect on the formulation's initial viscosity. Table 4 shows that most of the formulations that had magnesium aluminum silicate at or above 0.15%, had no sediment. While not wishing to be bound by theory, it is believed that magnesium aluminum silicate, is playing an important role in particle to particle interactions that is keeping the bismuth, as well as other components, suspended and/or enabling easier resuspension upon mixing/shaking.

The sedimentation can be determined by a visual observation method that can be performed as follows. The liquid pharmaceutical formulation is stored in a full PET bottle that can hold 8 fluid ounces (240 mL) for 30 days at 40° C. The bottles are stored closed in a room and not exposed to sunlight. The bottles are not shaken or moved during this period. After 30 days, the bottle is slowly inverted and a person looks through the bottle to see if any sedimentation is visually perceptible. As used herein, "visually perceptible" means that a human viewer can visually discern the sedimentation with the unaided eye (excepting standard corrective lenses adapted to compensate for near-sightedness, farsightedness, or stigmatism, or other corrected vision) in lighting at least equal to the illumination of a standard 100 watt incandescent white light bulb at a distance of 6 inches (15.24 cm).

In one example, the liquid formulation has no more than slight sedimentation that is visually perceptible. In another example, the liquid formulation has no sedimentation that is visually perceptible.

Table 5 shows the pH change at 0, 30, 60, 90, and 180 days when the liquid pharmaceutical product is stored at 40° C., 75% relative humidity (RH) for 180 days. Table 5B shows the composition of Examples 18 and 19.

TABLE 5B

|  | Examples 18-19 |
|---|---|
| BSS | 1.7305% |
| Suspension System | See Table 5A |
| Benzoic Acid | 0.025% |
| Salicylic Acid | 0.0749% |
| Sodium Salicylate | 0.0559% |
| Sweetener | 0.0612% |
| Color | 0.0124% |
| Flavor | 0.088% |
| Distilled Water | Q.S. |

The examples in Table 5A shows that Example 18, which was formulated without magnesium aluminum silicate, essentially eliminated the pH drift over a 180 day period when stored at 40° C. and 75% RH. Thus, in some circumstances it may be beneficial to formulate without magnesium aluminum silicate and use a suspension system that includes gellan gum and/or methyl cellulose. The pH drift in Example 19 can also lead to an improved shelf life over current formulations.

The pH can be calculated using the pH Test Method as described below. The solution is stored upright in closed PET bottles and are not exposed to sunlight.

Examples 20-25, as shown in table 6 below, were made as follows. First, three premixes or slurries were made. The dye premix was made by adding color to water and heating and stirring until dissolved.

Separately, a minors premix was made by adding the flavor, salicylic acid, sodium salicylate, sweeteners, benzoic acid, and sorbic acid to water and heating and stirring until the solution became clear.

Separately, a BSS slurry was made by adding BSS powder to water under high shear.

To make the examples, the first step was to add the minors premix to water. Then, the suspension system components were added to water under high shear mixing: gellan gum, magnesium aluminum silicate, and finally methyl cellulose. Then, under low shear mixing the dye premix and then the BSS slurry were added. Then Q.S. of water was added to form the final bismuth-containing pharmaceutical formulation.

TABLE 5A

| | | pH after being stored at 40° C./75% RH | | | | |
|---|---|---|---|---|---|---|
| Example | Suspension System | 0 days | 30 days | 60 days | 90 days | 180 days |
| 18 | 0.1% magnesium aluminum silicate, 1.086% methyl cellulose, 0.025% gellan gum | 3.5 | 3.8 | 3.9 | 3.9 | 4.0 |
| 19 | 1.086% methyl cellulose, 0.0375% gellan gum | 3.2 | 3.3 | 3.3 | 3.3 | 3.2 |

TABLE 6

|  | Ex. 20 | Ex. 21 | Ex. 22 | Ex. 23 | Ex. 24 | Ex. 25 |
|---|---|---|---|---|---|---|
| BSS | 1.716% | 1.716% | 1.716% | 1.716% | 1.716% | 1.716% |
| Methyl cellulose | 1.3% | 1.3% | 1.3% | 1.3% | 1.3% | 1.0% |
| Magnesium aluminum silicate | 0.11% | 0.11% | 0.11% | 0.22% | 0.11% | 0.22% |
| Gellan gum | 0.035% | 0.035% | 0.07% | 0.07% | 0.1% | 0.1% |
| Benzoic Acid | 0.0746% | 0.0746% | 0.0746% | 0.0746% | 0.0746% | 0.0746% |
| Sorbic Acid | 0.0373% | 0.0373% | 0.0373% | 0.0373% | 0.0373% | 0.0373% |
| Salicylic acid | 0.050% | 0.050% | 0.050% | 0.050% | 0.050% | 0.050% |
| Sodium Salicylate | 0.0847% | 0.0847% | 0.0847% | 0.0847% | 0.0847% | 0.0847% |
| Sweetener | 0.0612% | 0.0612% | 0.0612% | 0.0612% | 0.0612% | 0.0612% |
| Color | 0.0062% | 0.0062% | 0.0062% | 0.0062% | 0.0062% | 0.0062% |
| Flavor | 0.0888% | 0.0888% | 0.0888% | 0.0888% | 0.0888% | 0.0888% |
| Distilled Water | Q.S. | Q.S. | Q.S. | Q.S. | Q.S. | Q.S. | pH Test Method

First, calibrate the Thermo Scientific™ Orion™ 710A pH meter using the manufacturer's instructions for autocalibration. Select two buffer solutions for calibration whose difference in pH does not exceed 4 pH units (i.e. 1.68 and 4; 4 and 7). If it is necessary to measure samples whose pH encompass multiple ranges (i.e. 3.5 and 4.5) a three-point calibration curve is necessary.

Place a suitable quantity of a neat sample to be tested in a beaker at ambient temperature. Enough solution should be used to cover electrode tips and liquid junction completely. Lower the electrodes into position and stir with a magnetic stirbar while measuring the pH. Agitation should be vigorous enough to mix the solution thoroughly without whipping air into it.

After each usage the electrode should be washed free from the sample solution with deionized water. Blot the pH electrode with an absorbent tissue—do not rub. When not in use, store the electrode in storage solution recommended in the instruction manual or in buffer with a pH of less than 7 buffer and keep the internal solution filling port capped to reduce evaporation.

Rheology Test Method

TA Instrument AR 200 Rheometer (available from TA Instruments, New Castle, Del.) with a couette setup (cup and bob), Stainless Steel Standard DIN or concentric cylinder. The inner radius is 15.18 mm, the rotor outer radius is 14.01 mm, the cylinder immersed height is 42.02 mm, and the gap is 5920 μm.

The test is run at 25° C. with a 23 mL sample. The procedure is run with a stepped flow from 0.0100 $s^{-1}$ shear rate to 100.0 $s^{-1}$ shear rate at 10 points/decade.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All percentages and ratios used herein are by weight unless otherwise specified, and all measurements are made at 25° C. unless otherwise specified.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid pharmaceutical suspension for oral administration comprising:
   a. a bismuth-containing pharmaceutical agent;
   b. a suspension system comprising from about 0.01% to about 1% gellan gum; and
   c. water.

2. The liquid pharmaceutical suspension of claim 1 wherein the gellan gum comprises high acyl gellan gum.

3. The liquid pharmaceutical suspension of claim 1 wherein the suspension system further comprises from about 0.1% to about 5% methyl cellulose.

4. The liquid pharmaceutical suspension of claim 1 wherein the suspension system comprises from about 0.01% to about 1% magnesium aluminum silicate.

5. The liquid pharmaceutical suspension of claim 1 wherein the suspension system comprises from about 0.01% to about 0.75% gellan gum.

6. The liquid pharmaceutical suspension of claim 5 wherein the gellan gum comprises high acyl gellan gum.

7. The liquid pharmaceutical suspension of claim 6 comprising from about 0.2% to about 8% bismuth-containing pharmaceutical agent.

8. The liquid pharmaceutical suspension of claim 7 wherein the suspension system comprises from about 0.01% to about 0.6% magnesium aluminum silicate.

9. The liquid pharmaceutical suspension of claim 8 wherein the suspension system further comprises from about 0.1% to about 5% methyl cellulose.

10. The liquid pharmaceutical suspension of claim 5 wherein the suspension system comprises from about 0.01% to about 0.5% gellan gum.

11. The liquid pharmaceutical suspension of claim 9 wherein the suspension system comprises from about 0.015% to about 0.15% gellan gum.

12. The liquid pharmaceutical suspension of claim 11 wherein the suspension system comprises from about 0.02% to about 0.05% gellan gum.

13. The liquid pharmaceutical suspension of claim 1 further comprising a preservative comprising benzoic acid.

14. The liquid pharmaceutical suspension of claim 4 wherein the suspension system comprises from about 0.1% to about 0.8% magnesium aluminum silicate.

15. A liquid pharmaceutical suspension for oral administration comprising:
   a. a bismuth-containing pharmaceutical agent;
   b. a suspension system comprising from about 0.005% to about 1% gellan gum and from about 0.01% to about 1% magnesium aluminum silicate; and
   c. water.

16. The liquid pharmaceutical suspension of claim 15 wherein the suspension system further comprises about 0.1% to about 0.8% magnesium aluminum silicate.

17. The liquid pharmaceutical suspension of claim 16 wherein the suspension system further comprises a non-ionic cellulose ether polymer.

18. A liquid pharmaceutical suspension for oral administration comprising:
   a. a bismuth-containing pharmaceutical agent;
   b. a suspension system comprising from about 0.005% to about 1% gellan gum and from about 0.1% to about 5% methyl cellulose; and
   c. water.

19. The liquid pharmaceutical suspension of claim 18 wherein the suspension system comprises from about 0.01% to about 0.5% gellan gum.

20. The liquid pharmaceutical suspension of claim 19 wherein the suspension system comprises from about 0.5% to about 1.5% methyl cellulose.

* * * * *